US007833990B2

(12) United States Patent
Matou et al.

(10) Patent No.: US 7,833,990 B2
(45) Date of Patent: Nov. 16, 2010

(54) USE OF LOW-MOLECULAR-WEIGHT HIGHLY SULFATED POLYSACCHARIDE DERIVATIVES FOR MODULATING ANGIOGENESIS

(75) Inventors: Sabine Matou, Montfermeil (FR); Sylvia Colliec-Jouault, Nantes (FR); Dominique Helley, Paris (FR); Jacqueline Ratiskol, Sainte Luce sur Loire (FR); Corinne Sinquin, Nantes (FR); Claire Boisset, Roscoff (FR); Jean Guezennec, Plouzane (FR); Anne-Marie Fischer, Paris (FR)

(73) Assignees: Institut Francais de Recherche pour l'Exploitation de la Mer (IFREMER), Issy les Moulineaus (FR); Universite Rene Descartes Paris 5, Paris (FR)

( * ) Notice: Subject to any disclaimer, the term of this patent is extended or adjusted under 35 U.S.C. 154(b) by 245 days.

(21) Appl. No.: 11/629,544

(22) PCT Filed: Jun. 6, 2005

(86) PCT No.: PCT/FR2005/001378

§ 371 (c)(1),
(2), (4) Date: Dec. 13, 2006

(87) PCT Pub. No.: WO2006/003289

PCT Pub. Date: Jan. 12, 2006

(65) Prior Publication Data

US 2007/0259833 A1 Nov. 8, 2007

(30) Foreign Application Priority Data

Jun. 14, 2004 (FR) .................................. 04 06405

(51) Int. Cl.
*A61K 31/737* (2006.01)
*C07H 1/00* (2006.01)
(52) U.S. Cl. ..................................... 514/54; 536/123.1
(58) Field of Classification Search .................. 514/54; 536/123.1
See application file for complete search history.

(56) References Cited

U.S. PATENT DOCUMENTS

| 5,985,330 | A * | 11/1999 | Collin .......................... 424/520 |
| 6,255,296 | B1 * | 7/2001 | Daniels ........................ 514/56 |
| 6,545,145 | B1 | 4/2003 | Rougeaux et al. |
| 6,828,307 | B1 | 12/2004 | Colliec-Jouault et al. |
| 2005/0245736 | A1 | 11/2005 | Oreste et al. |
| 2005/0256079 | A1 | 11/2005 | Oreste et al. |
| 2006/0014718 | A1 | 1/2006 | Oreste et al. |

FOREIGN PATENT DOCUMENTS

| EP | 0221977 | 5/1987 |
| FR | 2701488 | 8/1994 |
| FR | 2755142 | 4/1998 |
| JP | 10 218902 | 8/1998 |

OTHER PUBLICATIONS

Guezennec et al, Carbohydrate Polymers, 1999, 37, 19-24.*
Zhu, W.H. et al, American Journal of Pathology, 2002, 161 (3), 823-30.*
Matou et al, Thrombosis Research, 2002, 106, 213-221.*
Luyt et al, The Journal of Pharmacology and Experimental Therapeutics, 2003, 305(1), 24-39.*
Aymard et al., Rheological properties in aqueous media of three new bacterial polysaccharides from marine origin. *Food Hydrocolloids.* 5(1/2): 167-9 (1991).
Belcher et al., The determination of glucosamine. 79: 201-208 (1953).
Chabut et al., Low molecular weight fucoidan and heparin enhance the basic fibroblast growth factor-induced tube formation of endothelial cells through heparan sulfate-dependent alpha6 overexpression. *Mol Pharmacol.* 64: 696-702 (2003).
Colliec-Jouault et al., Characterization, chemical modifications and in vitro anticoagulant properties of an exopolysaccharide produced by *Alteromonas infernos. Biochem. Biophys. Acta.* 1528: 141-51 (2001).
Derwent Publications Ltd., London, GB, Database WPI Section Ch, Class B04, An 1998-501676, XP002368826.
Detillieux et al., Biological activities of fibroblast growth factor-2 in the adult myocardium. *Cardiovasc. Res.* 57: 8-19 (2003).
Espevik et al., A highly sensitive cell line, WEHI 164 clone 13, for measuring cytotoxic factor/tumor necrosis factor from human monocytes. *J. Immunol. Meth.* 95: 99-105 (1986).
Filisetti-Cozzi et al., Measurement of uronic acids without interference from neutral sugars. *Anal. Biochem.* 197: 157-62 (1991).
Giraux et al., Modulation of human endothelial cell proliferation and migration by fucoidan and heparin. *Eur. J. Cell. Biol.* 77: 352-9 (1998).
Guezennec et al., Deep-sea hydrothermal vents: a new source of innovative bacterial exopolysaccharides of biotechnological interest?. *J. Ind. Microb. Biotech.* 29: 204-8 (2002).
Guezennec et al., Preliminary chemical characterization of usual eubacterial exopolysaccharides of deep-sear origin. *Carbohydr. Polymers.* 24: 287-94 (1994).
Guezennec et al., Sulfation and depolymerization of a bacterial exopolysaccharide of hydrothermal origin. *Carbohydr. Polym.* 37: 19-24 (1998).

(Continued)

*Primary Examiner*—Shaojia Anna Jiang
*Assistant Examiner*—Ganapathy Krishnan
(74) *Attorney, Agent, or Firm*—Marshall, Gerstein & Borun LLP

(57) ABSTRACT

The invention relates to the use of certain low-molecular weight highly sulphated polysaccharide derivatives obtained from a bacterial polysaccharide for preparing a pharmaceutical composition suitable for modulating angiogenesis, particularly for use in accelerating vascular endothelial repair with a low haemorrhage risk in the event of thrombotic injuries.

24 Claims, No Drawings

OTHER PUBLICATIONS

Heba et al., The time course of tumor necrosis factor-alpha, inducible nitric oxide synthase and vascular endothelial growth factor expression in an experimental model of chronic myocardial infarction in rats. *J. Vasc. Res.* 38: 288-300 (2001).

Heilmann et al., Collateral growth: cells arrive at the construction site. *Cardiovasc. Surg.* 10: 570-8 (2002).

Kamerling et al., Characterization by gas-liquid chromatography-mass spectrometry and proton-magnetic-resonance spectroscopy of pertrimethylsilyl methyl glycosides obtained in the methanolysis of glycoproteins and glycopeptides. *Biochem. J.* 151: 491-5 (1975).

Luyt et al., Low-molecular-weight fucoidan promotes therapeutic revascularization in a rat model of critical hindlimb ischemia. *J. Pharmacol. Exp. Ther.* 305: 24-30 (2003).

Marti et al., Angiogenesis in ischemic disease. *Thromb. Haemost.* 82: 44-52, Suppl. 1, (1999).

Matou et al., Effect of fucoidan on fibroblast growth factor-2-induced angiogenesis in vitro. *Thromb Res.* 106: 213-21 (2002).

McNeil et al., Growth factors are released by mechanically wounded endothelial cells. *J. Cell. Biol.* 109: 811-22 (1989).

Montreuil et al., Glycoproteins in: Carbohydrate analysis, a practical approach, IRL Press, Oxford, Chapter 5: 143-204 (1986).

Nishino et al., Anticoagulant and antithrombin activities of oversulfated fucans. *Carbohydr. Res.* 229: 355-63 (1992).

Raguenes et al., Alteromonas infernus sp. nov., a new polysaccharide-producing bacterium isolated from a deep-sea hydrothermal vent. *J. Appl. Microbiol.* 82: 422-30 (1997).

Raguenes et al., Description of a new polymer-secreting bacterium from a deep-sea hydrothermal vent, *Alteromonas macleodii* subsp. *fijiensis*, and primary characterization of the polymer. *Appl. Environ. Microbiol.* 62(1): 67-73 (1996).

Raguenes et al., *Vibrio diaboliuc* sp. nov., a new polysaccharide-secreting organism isolated from a deep-sea hydrothermal vent polychaete annelid, *Alvinella pompejana*. *Int. J. System. Bacteriol.* 47(4): 989-95 (1997).

Rimington, The carbohydrate complex of the serum proteins: Improved method for isolation and re-determination of structure. Isolation of glucosaminodimannose from proteins of ox blood. *Biochem. J.* 25: 1062-71 (1931).

Rusnati et al., Interaction of angiogenic basic fibroblast growth factor with endothelial cell heparan sulfate proteoglycans. Biological implications in neovascularization. *Int. J. Clin. Lab. Res.* 26: 15-23 (1996).

Van Dedem et al., Determinations of the molecular mass of low molecular mass (LLM) heparin. *Pharmeuropa.* 3: 202-18 (1990).

Vivier et al., Signaling function of reconstituted CD16: receptor complex isoform. *Int. Immunol.* 4(11): 1313-23 (1992).

Weichelman et al., Investigation of the bicinchoninic acid protein assay: Identification of the groups responsible for color formation. *Anal. Biochem.* 175: 231-7 (1988).

Zubkov et al., Structure of the capsular polysaccharide from *Alteromonas* sp. CMM 155. *Carbohydr. Res.* 275: 147-54 (1995).

Combined International Search Report and Written Opinion, PCT/FR2005/001378, Mar. 3, 2006.

\* cited by examiner

USE OF LOW-MOLECULAR-WEIGHT HIGHLY SULFATED POLYSACCHARIDE DERIVATIVES FOR MODULATING ANGIOGENESIS

The present application is filed under 35 U.S.C. §371 as a U.S. national phase application of PCT application no. PCT/FR2005/001378, which was filed Jun. 6, 2005. The aforementioned PCT application claimed benefit of priority of French Patent Application No. 0406405, which was filed Jun. 14, 2004. The entire text of each of the aforementioned applications is incorporated herein by reference.

The present invention relates to the use of certain low-molecular-weight highly sulfated polysaccharide derivatives obtained from a polysaccharide of bacterial origin, for the preparation of a pharmaceutical composition for use in modulating angiogenesis, that can be used in particular for accelerating vascular endothelial repair with low hemorrhagic risk in the event of thrombotic events.

Heparin, a sulfated polysaccharide extracted from mammalian mucosa, is the antithrombotic agent most commonly used in the prevention and treatment of venous thrombosis. However, in the course of heparin treatments, side effects such as an allergic reaction or a hemorrhagic complication may occur (due to its high anticoagulant activity). In addition, heparin has been found to be relatively inactive in the prevention and treatment of arterial thrombosis. Because of the limits to the therapeutic use of heparin, it is important to be able to provide novel polysaccharides (for example, fucans, fucosylated chondroitin sulfate, exopolysaccharides, etc.) of nonmammalian origin (so as to avoid any risk of transmission of nonconventional agents), that have a low anticoagulant activity (in order to decrease the hemorrhagic risk) and are effective in combating arterial thrombosis.

The objectives are to prevent and treat arterial thrombosis and the consequences thereof. Specifically, when an arterial vascular lesion occurs, the absence of a monolayer of endothelial cells triggers platelets aggregation, followed by the formation of a thrombus. This arterial thrombus can obstruct the lumen of the blood vessel and thus prevent any oxygenation of the downstream tissue liable to result in a necrosis. Faced with this risk, it would be advantageous to be able to promote vascular endothelial repair and to stimulate collateral vascular circulation formation, two cellular events that originate from the stimulation of angiogenesis.

Angiogenesis is a complex, physiologically regulated process that results in the formation of new blood vessels from the pre-existing vascular network. It is during the pathological situations previously described (vascular endothelial lesion or hypoxia) that the amount of certain angiogenic factors, such as basic fibroblast growth factor (FGF-2) or vascular endothelial growth factor (VEGF), becomes much greater in the perivascular environment. Specifically, FGF-2 is mainly released after a vascular endothelial lesion, whereas VEGF is mainly synthesized by the cells in a hypoxic situation. These two factors, FGF-2 and VEGF, trigger the angiogenic process by acting on the endothelial cells, which is reflected by a stimulation of the three main steps of angiogenesis: migration, proliferation and differentiation of endothelial cells so as to form neovessels (Folkman J., Nat. Med., 1995, 1, 27-31; Detillieux K. A. et al., Cardiovasc. Res., 2003, 57, 8-19; Heilmann C. et al., Cardiovasc. Surg., 2002, 10, 570-578; McNeil P. L. et al., J. Cell Biol., 1989, 109, 811-822; Heba G. et al., J. Vasc. Res., 2001, 38, 288-300 and Marti H. H. and Risau W. et al., Thromb. Haemost., 1999, 82 (Suppl. 1), 44-52).

Prior studies have shown that sulfated polysaccharides (such as heparin or fucan) or nonsulfated polysaccharides (such as, for example, hyaluronic acid) can, depending on the experimental conditions, modulate angiogenesis induced by an angiogenic growth factor. These polysaccharides are rich in negatively charged chemical groups (sulfate and carboxylic groups) allowing them to interact with a large number of positively charged proteins, including certain matrix proteins (basal membrane, extracellular matrix), certain coagulation factors, and growth factors (such as, for example, FGF-2 and VEGF) and their high affinity receptors which are proteins known to be involved in angiogenesis (Giraux J. L. et al., Eur. J. Cell Biol., 1998, 77, 352-359; Matou S. et al., Thromb. Res., 2002, 106, 213-221; Chabut D. et al., Mol. Pharmacol., 2003, 64, 696-702; Luyt C. E. et al., J. Pharmacol. Exp. Ther., 2003, 305, 24-30). These growth factors belong to the family of heparin-binding growth factors (or HBGFs). These polyanionic soluble polysaccharides can modulate the interaction of the angiogenic factor with its high-affinity receptors (inducing signal transduction) or low-affinity receptors (cofactor for the high-affinity receptors), present at the surface of endothelial cells. Thus, the polysaccharide can potentiate the effect of the angiogenic factor by catalyzing the binding of several molecules to high-affinity receptors, which amplifies the dimerization of the latter. This receptor dimerization triggers signal transduction, thus stimulating the expression of the genes involved in the migration, proliferation and differentiation of endothelial cells. In this situation, the sulfated polysaccharide acts as a cofactor just like membrane-bound heparan sulfate proteoglycan (low-affinity site) (Rusnati M. and Presta M., Int. J. Clin. Lab. Res., 1996, 26, 15-23; Soker S. et al., Biochem. Biophys. Res. Commun., 1994, 203, 1339-47). Conversely, the sulfated polysaccharide can interfere in the binding of the angiogenic factor to the heparan sulfate proteoglycan by charge competition, thus preventing the induction of a cellular response.

The exopolysaccharide (EPS) called GY 785 is a polysaccharide produced by the bacterium *Alteromonas infernus* which is described in patent FR 2 755 142 and also in the article by Raguenes G. et al., J. Appl. Microbiol., 1997, 82, 422-30. The EPS GY 785 consists of a heterogeneous population of molecules with a high average molecular weight, i.e. of molecular weight greater than $1 \times 10^6$ g/mol. The EPS GY 785 is not very highly sulfated (sulfate content of less than 10% by weight); it consists of neutral monosaccharides (predominantly glucose and galactose) and of acidic monosaccharides (glucuronic acid and galacturonic acid); it does not comprise any amino sugars or acetate, lactate, pyruvate and succinate substituents; its protein content is approximately 4% by weight (Guezennec J., Ind. Microb. Biotech., 2002, 29, 204-208).

The EPS GY 785 is difficult to use in its native form in therapy, because of its high molecular weight and its size heterogeneity which result in a poor solubility and which make active preparations very difficult to characterize and to obtain reproducibly.

In recent studies, the inventors have developed a process for preparing low-molecular-weight sulfated derivatives, comprising a first step consisting of sulfation of the EPS GY 785, and then a second step consisting of depolymerization of the oversulfated EPS GY 785 by acid hydrolysis or by free-radical depolymerization, so as to obtain depolymerized derivatives having a sulfate content of 20% or 40% by weight (Guezennec J. et al., Carbohydr. Polym., 1998, 37, 19-24). Unlike the native product, the derivatives obtained after chemical modification of the EPS GY 785 exhibit anticoagulant activities (Colliec-Jouault S. et al., Biochim. Biophys. Acta 1528, 2001, 141-151).

The inventors have also shown that the free-radical depolymerization, obtained by the action of hydrogen peroxide in the presence of copper acetate, results, in a single step, in low-molecular-weight derivatives, generally of less than 25 000 g/mol, with a constant composition (low molecular-weight polydispersity) and with yields that are much higher than those obtained with the acid hydrolysis depolymerization process. The reaction takes place via the formation of free radicals derived from the reaction of a metal ion ($Cu^{2+}$ or $Fe^{3+}$) with hydrogen peroxide (Van Dedem G. and Nielsen J. I., Pharmeuropa, 1990, 3, 202-218). These free radicals are very reactive and capable of degrading, at neutral pH, the polysaccharides more effectively than acid hydrolysis.

The inventors have in particular previously shown that chemical sulfation, carried out according to the conditions of T. Nishino and T. Nagumo (Carbohydr. Res., 1992, 229, 355-362), produces derivatives having a sulfate content greater than that of the native EPS GY 785 (20% to 40% by weight of sulfate against 10% by weight of sulfate, respectively). The anticoagulant activity increases as a function of the sulfate content and this activity disappears if the sulfate content is less than 20% by weight.

The inventors have now discovered that certain sulfated and depolymerized polysaccharide derivatives of the EPS GY 785 (obtained according to a preparation process comprising a first step consisting of sulfation of the native EPS GY 785 so as to obtain an oversulfated EPS GY 785 derivative having a sulfate content of less than or equal to 45% by weight, and then a second step consisting of free-radical depolymerization of the oversulfated EPS GY 785 derivative obtained in the previous step, so as to produce a polysaccharide derivative having a molecular weight of less than or equal to 25 000 g/mol) have an activity on the modulation of angiogenesis.

The first subject of the present invention is thus the use of sulfated polysaccharide derivatives having a molecular weight of less than or equal to 25 000 g/mol, a polydispersity index of less than 2 and a degree of sulfate-group substitution of less than or equal to 45%, and preferably of between 30% and 45%, inclusive, said derivatives being obtained according to a preparation process comprising at least the following steps:

a first step consisting of chemical sulfation, comprising:
  a) a first substep consisting of dissolution, in an anhydrous solvent, of a lyophilized GY 785 polysaccharide produced by the marine bacterium *Alteromonas infernus*, and
  b) a second substep consisting of addition, at a temperature of between 45 and 60° C., of at least one chemical sulfation agent in an amount sufficient to produce a sulfated polysaccharide having a degree of sulfate-group substitution of less than or equal to 45% by weight relative to the total weight of the sulfated GY 785 polysaccharide;
a second step consisting of free-radical depolymerization of the sulfated polysaccharide obtained in the previous step, so as to produce a sulfated polysaccharide having a molecular weight of less than or equal to 25 000 g/mol and a polydispersity index of less than 2, for the preparation of a pharmaceutical composition for use in modulating angiogenesis.

The sulfated polysaccharide derivatives obtained according to the process used in accordance with the invention exhibit a good size homogeneity (polydispersity index: I(Mw/Mn)<2 with Mw=weight-average molecular weight and Mn=number-average molecular weight), without it being necessary to carry out a supplementary fractionation by steric exclusion.

In the first step, the lyophilized EPS GY 785 can be used in the native state or in the form of an addition salt with a weak or strong base, that may, for example, be chosen from pyridine, triethylamine, tributylamine, tetrabutylammonium hydroxide and sodium hydroxide.

According to a preferred embodiment of the process used in accordance with the invention, the EPS GY 785 used in the first step is preferably in the form of a lyophilized addition salt with a base. This lyophilized salt can, for example, be prepared by elution of an aqueous solution of EPS GY 785 at a concentration of between 1 and 8 mg/ml on a column of ion exchange resin such as, for example, those sold under the name Dowex® by the company Dow Chemical; the EPS GY 785 is placed in the $H^+$ form. The eluate is collected as long as the pH remains acidic, and then the pH is subsequently adjusted to approximately 6.5 with the desired base as defined above. The EPS GY 785 in the form of a salt is then ultrafiltered and lyophilized.

The anhydrous solvents that may be used in the first step are preferably chosen from dimethylformamide (DMF), dimethyl sulfoxide (DMSO) and formamide.

The amount of EPS GY 785 present in the anhydrous solvent may be between approximately 1 and 10 mg/ml, preferably between approximately 1 and 5 mg/ml, and even more preferably this amount is approximately 5 mg/ml.

In substep a), the dissolution of the EPS GY 785 in the anhydrous solvent is preferably carried out, with stirring, at ambient temperature for approximately 1 to 2 hours and then at a temperature of between 40 and 50° C., preferably at a temperature of approximately 45° C., for approximately 2 hours under argon with molecular sieve.

The chemical sulfation agent(s) used in substep b) can be added to the solution of EPS GY 785 in dry form or in the form of a solution in the same anhydrous solvent as that used to dissolve the EPS GY 785.

The chemical sulfation agents are preferably chosen from complexes of pyridine sulfate (free or coupled to a polymer), of triethylamine sulfate and of trimethylamine sulfate. In substep b), the chemical sulfation agent(s) is (are) added to the solution of EPS GY 785 in a weight amount preferably representing from approximately 4 to 6 times, and even more preferably approximately 5 times, the mass of the EPS GY 785 in solution.

The chemical sulfation reaction is then preferably carried out with stirring for a period of between approximately 2 and 24 hours depending on the desired degree of sulfation.

When the desired degree of sulfation is reached, the sulfation reaction is stopped, after cooling of the reaction medium:
  either by addition of water in a proportion preferably equal to 1/10 of the reaction volume and adjustment of the pH of the reaction medium to 9 with a basifying agent such as, for example, sodium hydroxide (3 M);
  or, and preferably, by precipitation in the presence of sodium chloride-saturated acetone or of methanol and then dissolution of the precipitate in water.

According to a specific embodiment of the process in accordance with the invention, the solution of sulfated EPS GY 785 is preferably then dialyzed so as to eliminate the various salts, and then lyophilized.

The second step consisting of free-radical depolymerization of the sulfated EPS GY 785 obtained at the end of the first step is preferably carried out by addition, to the reaction mixture comprising the sulfated EPS GY 785 in the presence of a metal catalyst, of a solution of an oxidizing agent, preferably chosen from peroxides such as hydrogen peroxide and peracids such as peracetic acid and 3-chloroperbenzoic acid; said addition being carried out continuously and with stirring for a period of between 30 minutes and 10 hours; the reaction mixture preferably being maintained at a pH of between 6 and 8 by the continuous addition of a basifying agent such as sodium hydroxide, and at a temperature of between approximately 30 and 70° C. throughout the free-radical depolymerization reaction.

During this step, the oxidizing agent is preferably a solution of hydrogen peroxide ($H_2O_2$). In this case, the solution of oxidizing agent is preferably added at a flow rate of between V1/1000 and V1/10 ml/minute, V1 being the volume of the reaction medium containing the sulfated derivative of EPS GY 785, to which the solution of oxidizing agent is added.

According to another preferred embodiment of the present invention, the solution of oxidizing agent used in the second step is a solution of hydrogen peroxide that has a concentration of between approximately 0.1% and 0.5% by weight, preferably of the order of 0.1% to 0.2% by weight, and that is added to the reaction mixture at a flow rate of between V1/50 and V1/500 ml/minute, preferably of the order of V1/100 ml/minute.

In this second step consisting of depolymerization, and according to a preferred embodiment of the present invention, the sulfated EPS GY 785 is present in the reaction mixture at a concentration of between approximately 2 and 10 mg/ml of reaction mixture.

The metal catalysts that can be used in the depolymerization step are preferably chosen from $Cu^{++}$, $Fe^{++}$ and $Cr^{+++}$ ions and the $Cr_2O_7^{2-}$ anion, as described in particular in patent application EP-A-0 221 977.

According to a preferred embodiment of the present invention, the metal catalyst is present in the reaction mixture at a concentration of between approximately $10^{-3}$ M and $10^{-1}$ M, and even more preferably at a concentration of between approximately 0.001 and 0.05 M.

When the reaction has ended, the process used in accordance with the invention can also comprise an additional step consisting of reduction of the polysaccharide derivatives obtained, using a reducing agent, so as to stabilize the chains, the reducing ends of which are very reactive, and in particular so as to prevent chain hydrolysis by the "peeling" reaction.

The nature of the reducing agents that can be used to this effect is not essential. It may in particular be sodium borohydride.

When the reactions have ended, the polysaccharide derivatives resulting from the depolymerization can be recovered by any suitable technique well known to those skilled in the art, such as, for example, by membrane ultrafiltration.

The free-radical depolymerization process in accordance with the invention and as described above makes it possible to obtain, in a single step, without preparative fractionation by steric exclusion chromatography, and with a good yield, very homogeneous sulfated polysaccharide derivatives with a molecular weight of less than or equal to 25 000 g/mol.

In the context of the disclosure of the present invention, the term "homogeneous derivative" is intended to mean a derivative that, in high-performance steric exclusion chromatography, exhibits a single main peak representing a predominant population of polysaccharide chains that are homogeneous with respect to size characterized by an Mc=chromatographic mass or mass at the peak close to 20 000 and a polydispersity index (calculated by taking the Mw/Mn ratio) of less than 2, and preferably of between 1.5 and 2.

As is demonstrated in the examples that follow, the derivatives thus obtained exhibit an angiogenesis-modulating activity. They make it possible in particular to promote vascular endothelial repair with a weak anticoagulant effect.

The pharmaceutical composition containing the polysaccharide derivatives obtained in accordance with the invention can also be used in combination with one or more growth factors present in said pharmaceutical composition or present in a different pharmaceutical composition that will then be administered separately, i.e. before, simultaneously or after the administration of the pharmaceutical composition containing the polysaccharide derivatives. Such growth factors can in particular be chosen from FGF, VEGF, HGF (hepatocyte growth factor) and PGF (placenta growth factor).

Given their angiogenesis-modulating properties, the polysaccharide derivatives as defined above can be used for the preparation of a pharmaceutical composition with pro-angiogenic activity, more particularly for use in cardiovascular therapy, said composition making it possible in particular to promote revascularization and vascular remodeling and to prevent and/or treat ischemia.

The pharmaceutical compositions obtained in accordance with the invention are preferably intended to be administered generally (orally, subcutaneously or intravenously). They can also be administered locally, in the form of gels, creams, ointments, lotions, etc.

They can also be administered in situ by means of substrates, of resorbable or nonresorbable devices, such as, for example, delayed-release supports, or slowly disintegrating sponges.

The present invention will be understood more fully from the further description that follows, and that refers (i) to an example of preparation of sulfated polysaccharide derivatives from the EPS GY 785 (EPS SDR) produced by the marine bacterium of hydrothermal origin *Alteromonas infernus*, by carrying out the process as defined above, (ii) to an example concerning the effect of an EPS SDR derivative on FGF-2-induced endothelial cell proliferation, (iii) to an example concerning the effect of an EPS SDR derivative on VEGF-induced endothelial cell proliferation, (iv) to an example demonstrating the effect of the EPS SDR on FGF-2-induced or VEGF-induced endothelial cell migration, and (v) to examples that study the effect of the EPS SDR on FGF-2-induced or VEGF-induced endothelial cell differentiation.

It should be clearly understood, however, that these examples are given only by way of illustration of the subject of the invention of which they in no way constitute a limitation.

EXAMPLE 1

Preparation of a Low-Molecular-Weight Highly Sulfated EPS GY 785 Derivative

1) Chemical Sulfation of the EPS GY 785

500 mg of lyophilizate of EPS GY 785 produced by the marine bacterium of hydrothermal origin *Alteromonas infernus*, according to the process described in example 1 of patent FR 2 755 142, were dissolved in 100 ml of anhydrous DMF with gentle stirring (250 rpm) for 2 hours at ambient temperature, and then for 2 hours at a temperature of 45° C.

When the dissolution was complete, 2.5 g of pyridine-$SO_3$ complex sold under the reference 84737 by the company Fluka (i.e. 5 times the mass of the GY 785 polysaccharide) were added to the reaction medium. The temperature of the mixture was then brought to and maintained at 45° C. for 2 hours with stirring. The reaction mixture was transferred into a beaker. The reaction was then stopped by the addition of 40 ml of water and the pH was then brought to 9 with 3M sodium hydroxide. The reaction mixture was then dialyzed in a dialysis bag having a cutoff threshold of between 12 000 and 16 000 Da, against tap water (overnight with running water), and then three times for 24 hours against Milli-Q water.

After dialysis, the solution containing the sulfated EPS GY 785 was frozen and lyophilized.

2) Free-Radical Depolymerization and Reduction with Sodium Borohydride 400 mg of sulfated EPS GY 785 obtained above in the previous step were dissolved in 95 ml of water. After dissolution, 2 ml of a catalytic solution containing 36 mg of copper acetate monohydrate ($10^{-3}$ M) were added. The temperature of the reactor was then brought to 60° C. and the pH was adjusted to 7.5 by the addition of 1 M sodium hydroxide. A 0.115% (v/v) solution of hydrogen peroxide was then added at a flow rate of 1 ml per minute, and the pH was regulated at around 7.5 by the addition of 1 M sodium hydroxide. The reaction was stopped after 1 hour.

The reduction was carried out at the end of depolymerization, by adding sodium borohydride (270 mg of $NaBH_4$ dissolved in 10 ml of water) to the reactor. The reduction was carried out with stirring for 2 hours at ambient temperature. The reduction was stopped by the addition of 10 N acetic acid, which makes it possible to eliminate the excess $NaBH_4$ remaining in the form of hydrogen gas given off. The solution was then filtered through a Büchner funnel with filters made of glass microfibers (porosity 3 µm). The filtered solution was eluted on a Chelex® 20 column (Biorad) in order to eliminate the residual copper. The decontaminated solution was then ultrafiltered through a cassette (cutoff threshold 1000 Da) and then lyophilized.

3) Characterization of the Sulfated and then Depolymerized Derivative of EPS GY 785 (EPS SDR); Comparison with the Native EPS GY 785

The molecular weights (Mc: chromatographic molecular weight determined at the summit of the peak; Mw and Mn) and the polydispersity (I=Mw/Mn) of the sulfated and then depolymerized EPS GY 785 derivative obtained above were determined by high-performance steric exclusion chromatography (HPSEC) on a Kontron system, in 0.1 M aqueous ammonium acetate at a flow rate of 0.5 ml/min using a Superdex® 200 column (Pharmacia). The column was calibrated with polysaccharide standards as follows: pullulans: 853 000-5800 g/mol (Polymer Laboratories, Interchim), dextran: 1500 g/mol; melezitose: 522 g/mol (Fluka), sucrose: 342 g/mol; glucose: 180 g/mol (Sigma). The results are analyzed using the Aramis® software (JMBS Développement, Le Fontanil, France).

The neutral monosaccharide content was determined by the method of Tillmans and Philippi (Analyt. Chem., 1929, 28, 350-) modified by Rimington (Biochem. J., 1931, 25, 1062-1071).

The uronic acid content was established using a modification of the m-hydroxydiphenyl-$H_2SO_4$ method (Filisetti-Cozzi and Carpitta, Anal. Biochem., 1991, 197, 157-162) and using glucuronic acid as standard. Interference from neutral hexoses was avoided by using potassium sulfamate and by carrying out controls comprising all the reagents with the exception of the m-hydroxydiphenyl.

The neutral and acidic monosaccharide contents were determined by gas chromatography. The analysis of the glycoside residues in the form of trimethylsilylated derivatives was carried out according to the method of Kamerling et al. (Biochem. J., 1975, 151, 491-495) and modified by Montreuil et al. (Glycoproteins In: Carbohydrate analysis, a practical approach, 1986, Chaplin M. F. and Kennedy J. F. (eds), IRL Press, Oxford, 143-204).

The contents of total sulfates (free plus bound to the sulfated then depolymerized derivative of EPS GY 785 and native EPS GY 785) were determined by elemental analysis of sulfur (S %) and by applying the following relationship: percentage of sulfate groups (%)=3.22×S %. The amount of free sulfates is quantified by ion exchange chromatography on a Dionex® DX-500 system connected to a conductimeter and according to the method described by the manufacturer Dionex. The result obtained makes it possible to calculate the amount of sulfates really bound to the EPS derivative, which is equal to the amount of total sulfates (obtained by elemental analysis) minus the amount of free sulfates (obtained by ion exchange chromatography).

Fourier transform infrared spectroscopy (FT-IR) was carried out on a Vector 22 having a resolution of 4 $cm^{-1}$. The infrared spectra of the polysaccharides were determined using KBr pellets (2 mg of polysaccharide are mixed with 200 mg of dry KBr), and all the infrared spectra were recorded at between 4000 and 400 $cm^{-1}$.

The anticoagulant activities of the sulfated then depolymerized EPS GY 785 derivative and of native EPS GY 785 were determined by measuring the activated cephalin time (ACT) using the ACT kit (Organon Teknika). To do this, 100 µl of a control buffer, or of dilutions of the sulfated then depolymerized EPS GY 785 derivative or of the native EPS GY 785 (0 to 100 µg/ml), are mixed with 100 µl of platelet-poor plasma (PPP) and 100 µl of the ACT reagent. The whole is incubated for 3 minutes at 37° C. The clot formation time is measured after the addition of 100 µl of a 25 mM solution of $CaCl_2$.

4) Results

The results obtained were combined in table I below:

TABLE I

| Characteristics | Sulfated and depolymerized derivative of EPS GY 785 (EPS SDR) | Native EPS GY 785 |
|---|---|---|
| Yield (%) | 70 | — |
| Total monosaccharides (g/100 g)[1] | 31 | 58 |
| Acidic monosaccharides (g/100 g)[1] | 20 | 29 |
| Rhamnose[2] | 1.7 | 2.7 |
| Mannose[2] | 1.6 | 2.8 |
| Fucose[2] | 0.5 | 1.3 |
| Xylose | 0.2 | 0.3 |
| Galactose[2] | 7.3 | 12.7 |
| Glucose[2] | 9.4 | 17 |
| Galacturonic acid[2] | 1.5 | 3.2 |
| Glucuronic acid[2] | 2.3 | 6 |
| Total - $SO_3Na$ (g/100 g)[3] | 40 | 10 |
| Bound $SO_3Na$ (g/100 g)[4] | 37 | — |
| Mc (g/mol) | 22 430 | >$10^6$ |
| Mw (g/mol) | 20 240 | — |
| Mn (g/mol) | 11 240 | — |
| I (Mw/Mn) | 1.8 | — |
| Anticoagulant activity[5] | 10-20 | inactive |

[1]colorimetric assays
[2]assay by gas chromatography
[3]assay by elemental analysis
[4]assay by ion exchange chromatography
[5]amount of polysaccharide in µg/ml of human plasma required to double the control coagulation time, ACT (control time = 40 seconds).

These results show that the sulfated then depolymerized derivative of EPS GY 785 is obtained with a good yield and that the monosaccharide contents are proportionally equivalent between the sulfated derivative and the native EPS that is naturally relatively nonsulfated. The sulfur content of the oversulfated product is 4 times greater than that of the native product. By virtue of free-radical depolymerization, a derivative of molecular weight (Mc and Mw) equal to 20 000 g/mol, that is homogeneous with respect to size (I<2) is obtained in 1 hour from the very high-molecular-weight (>$10^6$ g/mol) oversulfated EPS GY 785. Only the sulfated then depolymerized derivative of EPS GY 785 is anticoagulant; it doubles the control coagulation time for a concentration close to 15 μg/ml. By way of comparison, under the same conditions, 4 μg/ml of low-molecular-weight heparin and 1.5 μg/ml of unfractionated heparin are necessary in order to obtain this doubling. Thus, the sulfated then depolymerized derivative of EPS GY 785 is respectively 4 and 10 times less anticoagulant than a low-molecular-weight heparin or than an unfractionated heparin.

EXAMPLE 2

Effect of the Low-Molecular-Weight Highly Sulfated Derivative of EPS GY 785 on FGF-2-Induced Endothelial Cell Proliferation The effect of the low-molecular-weight sulfated derivative of EPS GY 785 (EPS SDR) in accordance with the invention and as prepared above in example 1, on the proliferation of endothelial cells extracted from human umbilical cord vein (HUVECs) was compared with that of the depolymerized native derivative (EPS DR), i.e. the derivative that was obtained by free-radical depolymerization.

a) Preparation of EPS DR

These derivatives were prepared from the lyophilizate of EPS GY 785 produced by the marine bacterium *Alteromonas infernus*, according to the process described in example 1 of patent FR 2 755 142.

The EPS DR was prepared according to a process using only the free-radical depolymerization step as described above in paragraph 2) of example 1.

The characteristics of the EPS DR derivatives were determined according to the methods described above in example 1 and are summarized in table II hereinafter:

TABLE II

| Characteristics | EPS DR |
|---|---|
| Total monosaccharides (g/100 g)[1] | 51 |
| Acidic monosaccharides (g/100 g)[1] | 38 |
| Total - $SO_3Na$ (g/100 g)[2] | 10 |
| Mc (g/mol) | 7800 |
| Mw (g/mol) | 17 300 |
| Mn (g/mol) | 6000 |
| I (Mw/Mn) | 2.8 |
| Anticoagulant activity[3] | Inactive |

[1]colorimetric assays
[2]assay by elemental analysis
[3]amount of polysaccharide in μg/ml of human plasma required to double the control coagulation time, ACT (control time = 40 seconds);
nd: not determined.

The EPS DR derivative is less sulfated than the SDR derivative. The HPSEC analysis indicates that the EPS DR derivative is less homogeneous with respect to size than the EPS SDR derivative, with a polydispersity of 2.8 against 1.8.

The polysaccharide chains that make up the EPS DR derivative are predominantly smaller (Mc=7800) than those of the EPS SDR derivative (Mc=22 430). The DR derivative has no coagulant activity, whereas the activity of the EPS SDR derivative has a coagulant activity for doubling the control coagulation time, ACT (control time=40 seconds), of 10-20 μg of product/ml of plasma.

b) Protocol

The HUVEC cells are seeded into wells coated with 0.5% gelatin. After incubation for 24 hours, the culture medium is changed: control medium alone (M199 culture medium (1 volume)+RPMI 1640 culture medium (1 volume), sold by the company Gibco-BRL, Cergy-Pontoise, France, supplemented with 5% of fetal calf serum sold by the company ATGC, Noisy-le-Grand, France) or enriched in FGF-2 at 5 ng/ml (sold by the company AbCys SA, Paris, France) or in EPS derivatives alone (10 μg/ml) or in FGF-2 (at 5 ng/ml)+ EPS derivatives (1 or 10 μg/ml). The medium is renewed every 2 days. After 3 days of treatment, the cells are detached and counted using a Malassez cell.

c) Results

The results are given in table III hereinafter:

TABLE III

| Growth factors and/or polysaccharides | Increase in cell proliferation (as % compared to FGF-2) |
|---|---|
| Control (without FGF-2) | 66.8 ± 53**** |
| FGF-2 | 100 |
| FGF-2 + EPS SDR (1 μg/ml) | 107.3 ± 1.4 |
| FGF-2 + EPS SDR (10 μg/ml) | 120.9 ± 5.2* |
| FGF-2 + EPS DR (1 μg/ml)[6] | 89.6 ± 2.9 |
| FGF-2 + EPS DR (10 μg/ml)[6] | 112.8 ± 6.9 |

[6]polysaccharides that are not part of the invention
*p < 0.05 and
****p < 0.0001

In table III above, each value represents the mean± the standard deviation of five determinations. For each experiment, the results are expressed as %, 100% corresponding to the cells treated with FGF-2 alone at 5 ng/ml.

These results show that, compared with the control (absence of growth factor and of polysaccharide) and with the addition of FGF-2 alone, a significant increase in cell proliferation is observed in the presence of FGF-2 and EPS SDR at the concentration of 10 μg/ml.

EXAMPLE 3

Effect of the EPS GY 785 SDR Derivative on VEGF-Induced Endothelial Cell Proliferation The effect of the derivative of EPS GY 785 as synthesized above in example 1 on VEGF-induced endothelial cell proliferation (VEGF sold by the company AbCys SA, Paris, France) was also studied according to the same protocol as that used above in example 2.

In this example, the VEGF was used at a concentration of 10 ng/ml and the HUVEC cells were detached and counted after 6 days of treatment.

The results obtained are given in table IV hereinafter:

TABLE IV

| Growth factors or polysaccharide | Increase in cell proliferation (as % compared to VEGF) |
| --- | --- |
| Control (without VEGF) | 59.5 ± 4.9**** |
| VEGF | 100 |
| VEGF + EPS SDR (10 µg/ml) | 137.6 ± 10.7** |

**$p < 0.01$ and
****$p < 0.0001$.

In table IV above, each value represents the mean± the standard deviation of 4 determinations. For each experiment, the results are expressed as %, 100% corresponding to the cells treated with VEGF alone at 10 ng/ml.

EXAMPLE 4

Demonstration of the Effect of EPS SDR on FGF-2-Induced or VEGF-Induced Endothelial Cell Migration 1) Protocol In this example, the EPS SDR derivative as prepared above in example 1 was used.

Angiogenic growth factors such as FGF-2 and VEGF exert a chemoattractive effect on endothelial cells, which triggers the migration of the latter. A system which demonstrates the oriented migration of endothelial cells induced by the angiogenic factor was used by the inventors. It is the Boyden chamber system. This system comprises two compartments: an upper chamber or insert containing a culture medium (culture medium identical to that which was described in b) of example 2 above) that is angiogenic factor-poor (FGF-2: 1 ng/ml; and VEGF: 1 ng/ml), and a lower chamber or well containing a culture medium identical to that of the upper chamber but rich in angiogenic factors (FGF-2: 10 ng/ml; and VEGF: 10 ng/ml), these two chambers being separated by a porous membrane. Endothelial cells are deposited onto the upper face of the porous membrane separating the two chambers. Under the effect of the angiogenic factor concentration gradient thus created between the two compartments, the endothelial cells are attracted to the compartment with the highest concentration of angiogenic factor (lower chamber).

The effect of the EPS SDR derivative, at 10 µg/ml, on the oriented migration of the endothelial cells was evaluated when added or not added to the two compartments of the Boyden chamber.

By virtue of this oriented migration and after 6 hours of incubation, some of the cells are located on the lower face of the membrane. Each condition was tested 3 times in duplicate each time. Only the cells that have migrated (located on the lower face) are fixed and stained with a view to counting under an optical microscope.

2) Results

In the presence of growth factors alone (FGF-2 or VEGF), i.e. without EPS SDR derivative, the migration of the cells is significantly increased by 40% ($p<0.0001$) compared to the control (migration of the cells from a culture medium containing neither growth factor nor EPS derivative). The addition of 10 µg/ml of the EPS SDR derivative to the FGF-2 significantly decreases by 20% ($p<0.05$) the migration of the cells compared to that induced by FGF-2 alone. The addition of the same derivative at the same concentration to VEGF does not modify the migration of the cells compared with that observed in the presence of VEGF alone.

EXAMPLE 5

Effect of EPS SDR on FGF-2-Induced Endothelial Cell Differentiation—Comparison With EPS DR In this example, the EPS SDR as prepared above in example 1 and also the EPS DR as prepared above in example 2 were used.

1) Protocols a) In vitro Angiogenesis on Matrigel®

Using an in vitro angiogenesis model, it was shown that fucan (a sulfated polysaccharide of a brown alga), unlike unfractionated heparin, potentiates the angiogenic effect of FGF-2 on human large-vessel endothelial cells (Matou et al., 2002, mentioned above).

The same experimental system as that used in the article by Matou et al. was used in this example for studying the effect of the EPSs with respect to FGF-2.

This system consists, firstly, in treating HUVEC endothelial cells with FGF-2, in the presence of the EPS derivative (EPS SDR or EPS DR) for 72 hours. For this, the cells are seeded into wells coated with 0.5% gelatin. The concentration of FGF-2 used is 5 ng/ml, the concentration most commonly used in in vitro models of angiogenesis, and that of the EPSs is 10 µg/ml.

The cells thus treated are then detached with Versene® (Gibco) and 0.01% collagenase and deposited (in the absence of polysaccharides and/or the angiogenic factor) onto a reconstituted basal membrane called Matrigel® sold by the company Becton Dickinson, Bedford, Mass., USA); this system makes it possible to evaluate the effect of the EPS tested on FGF-2-induced endothelial cell differentiation.

On contact with this basal membrane, the endothelial cells will (or will not) become organized into a tubular structure, depending on their degree of differentiation. After 18 hours of incubation at a temperature of 37° C., the cells are fixed with glutaraldehyde and then stained with Giemsa stain.

The length of the vascular tubes formed is quantified by image analysis using a measurement program (Mesurim® provided by the University of Amiens, http://www.ac-amiens.fr). For each well, 5 fields (4 quadrants and the center) are counted.

b) Overexpression of the α6 Integrin Subunits

It has previously been shown that the effect of a sulfated polysaccharide (fucan family) on HUVEC differentiation is accompanied by overexpression of the α6 integrin subunit (Matou et al., 2002, mentioned above). The overexpression of the α6 integrin subunit was quantified at the surface of the HUVEC endothelial cells cultured on gelatin in the absence or presence of FGF-2 and with or without EPS SDR derivative, and detached as described above. The quantification was carried out by flow cytometry. The cells were incubated for 30 minutes at a temperature of 4° C. with the anti-α6 antibody (sold by the company BD Biosciences & Pharmingen, San Diego, Calif., USA under the reference 555736). The cells were then analyzed by immunofluorescence on a FACSCalibur® flow cytometer (BD Biosciences).

2) Results

The results obtained are reported in table V hereinafter:

TABLE V

| Growth factors and/or polysaccharides | FGF-2-induced cell differentiation (as % compared to FGF-2) |
|---|---|
| Control (without FGF-2) | no tube formed |
| FGF-2 | 100 |
| FGF-2 + EPS SDR (10 μg/ml) | 156.2 ± 4.1** |
| FGF-2 + EPS DR (10 μg/ml)[6] | 109.6 ± 13.2 |

[6]derivative that is not part of the invention
**$p < 0.01$.

Each value represents the mean± the standard deviation of 3 determinations.

These results show that, in the absence of growth factor and of EPS derivatives (control), the cells do not form vascular tubes after 18 hours on Matrigel®. In the presence of FGF-2 alone, the cells become organized as vascular tubes so as to form a capillary-type three-dimensional vascular network. FGF-2 and the EPS SDR derivative added jointly to the cell culture make it possible to significantly increase the density of the network. Specifically, through the addition of a polysaccharide derivative obtained in accordance with the process as used according to the present invention to the cells treated with FGF-2, the total length of the tubular structures is significantly increased by 56% ($p < 0.01$) compared with that obtained in the presence of FGF-2 alone.

By way of comparison, no significant increase in FGF-2-induced vascular tube formation was obtained with the EPS DR derivatives obtained according to processes that are not part of the invention.

As regards the expression of the α6 integrin subunits, only the EPS SDR derivative obtained according to the process implemented according to the invention was tested. Treatment of the cells with FGF-2 alone induces a significant overexpression ($p < 0.0001$) of the α6 integrin subunits; this expression if 4 times greater than that of the control (untreated cells). The EPS SDR derivative in accordance with the invention, when added to FGF-2, significantly increases by 72% ($p < 0.001$) the expression of the α6 integrin subunit compared with that observed in the presence of FGF-2 alone. The EPS SDR derivative has no effect in the absence of FGF-2.

All these results show that only the EPS SDR derivative obtained according to the preparation process used in accordance with the invention, i.e. in which the chemical sulfation step precedes the free-radical depolymerization step, significantly and reproducibly potentiates the angiogenic effect of FGF-2.

EXAMPLE 6

Effect of the EPS SDR on VEGF-Induced Endothelial Cell Differentiation

1) Protocols a) In vitro Angiogenesis on Matrigel®

VEGF, another angiogenic factor that is also very important, is known to be more specific for endothelial cells than FGF-2. The study system set up to evaluate the effect of FGF-2 on endothelial cell differentiation on Matrigel® and as described above in example 5 does not make it possible to observe vascular tube formation in the presence of VEGF.

A change in protein support was therefore envisioned, and collagen type I (extracted from rat tail, sold by the company Biogenesis, Poole, UK) was chosen to replace the gelatin of the system described in example 5. As early as the day after the seeding of the HUVEC cells, the culture medium is changed and replaced with medium not enriched or enriched in VEGF (10 ng/ml) with or without EPS SDR at 10 μg/ml.

After 6 days of this treatment, the cells are detached with Versene® (Gibco) and 0.1% collagenase and then deposited onto Matrigel®. The tubular structures are observed as described in example 5 above.

b) Overexpression of the α6 Integrin Subunits

A quantification of the α6 integrin subunit was carried out by flow cytometry as described above in example 5.

2) Results

On Matrigel®, the cells not treated with VEGF in the presence or absence of EPS SDR derivative do not form tubular structures. In the presence of VEGF alone, the cells form a partial three-dimensional vascular network. The addition of the EPS SDR derivative to the VEGF increases the density of this network.

The treatment of the cells with VEGF significantly increases the expression of the α6 integrin subunit by a factor of 2 ($p < 0.01$), compared with the untreated cells. The addition of the EPS SDR derivative to this VEGF treatment significantly increases by 54% ($p < 0.001$) the expression of the α6 integrin subunit compared with that observed in the presence of VEGF alone.

All these results show that the EPS SDR derivative obtained according to a preparation process in which the sulfation step precedes the depolymerization step can be used for the preparation of a medicament for use in modulating angiogenesis.

What is claimed is:

1. A method of activating angiogenesis in a subject in need thereof, comprising administering to said subject a composition comprising a sulfated polysaccharide derivative of a GY 785 polysaccharide produced by the marine bacterium *Alteromonas infernus*, wherein the sulfated polysaccharide derivative has a molecular weight of less than or equal to 25,000 g/mol, a polydispersity index of less than 2 and a degree of sulfate-group substitution of less than or equal to 45%, and is obtained according to a preparation process comprising at least the following steps:

a first step consisting of chemical sulfation, comprising:
  a) a first substep consisting of dissolution, in an anhydrous solvent, of a lyophilized GY 785 (EPS GY 785) polysaccharide, and
  b) a second substep consisting of addition, at a temperature of between 45 and 60° C., of at least one chemical sulfation agent in an amount sufficient to produce a sulfated polysaccharide having a degree of sulfate-group substitution of less than or equal to 45% by weight relative to the total weight of the sulfated polysaccharide;

a second step consisting of free-radical depolymerisation of the sulfated polysaccharide obtained in the previous step, so as to produce a sulfated polysaccharide derivative having a molecular weight of less than or equal to 25,000 g/mol and a polydispersity index of less than 2, and wherein said composition is administered to said subject in a therapeutically effective amount, thereby activating angiogenesis in the subject.

2. The method of claim 1, wherein in the first step of the preparation process, the lyophilized EPS GY 785 polysaccharide is the native EPS GY 785 or in the form of an addition salt with a base.

3. The method of claim 2, wherein the lyophilized EPS GY 785 polysaccharide is used in the form of an addition salt with a strong or weak base chosen from pyridine, triethylamine, tributylamine, tetrabutylammonium hydroxide and sodium hydroxide.

4. The method of any one of claims 1-3, wherein the anhydrous solvent is chosen from dimethylformamide, dimethyl sulfoxide and formamide.

5. The method of claim 4, wherein the amount of EPS GY 785 polysaccharide present in the anhydrous solvent is between 1 and 10 mg/ml.

6. The method of claim 5, wherein the amount of EPS GY 785 polysaccharide present in the anhydrous solvent is between 1 and 5 mg/ml.

7. The method of claim 1, wherein in substep a), the dissolution of the lyophilized EPS GY 785 polysaccharide in the anhydrous solvent is carried out, with stirring, at ambient temperature for 1 to 2 hours and then at a temperature of between 40 and 50° C., for 2 hours under argon with molecular sieve.

8. The method of claim 1, wherein the at least one chemical sulfation agent used in substep b) is chosen from complexes of pyridine sulfate, of triethylamine sulfate and of trimethylamine sulfate.

9. The method of claim 8, wherein in substep b), the at least one chemical sulfation agent is added to the solution of EPS GY 785 polysaccharide in a weight amount representing from 4 to 6 times the mass of the EPS GY 785 polysaccharide in solution.

10. The method of claim 9, wherein the chemical sulfation reaction is carried out with stirring for a period of between 2 and 24 hours.

11. The method of claim 10, wherein the chemical sulfation reaction is stopped, after cooling of the reaction medium: either by addition of water in a proportion equal to 1/10 of the reaction volume and adjustment of the pH of the reaction medium to 9 with a basifying agent; or by precipitation in the presence of sodium chloride-saturated acetone or of methanol and then dissolution of the precipitate in water.

12. The method of claim 1, wherein the second step consisting of free-radical depolymerisation is carried out by addition, to the reaction mixture comprising the sulfated polysaccharide in the presence of a metal catalyst, of a solution of an oxidizing agent; said addition being carried out continuously and with stirring for a period of between 30 minutes and 10 hours.

13. The method of claim 12, wherein the reaction mixture is maintained at a pH of between 6 and 8 by the continuous addition of a basifying agent, and at a temperature of between 30 and 70° C., throughout the free-radical depolymerisation reaction.

14. The method of claim 12 or 13, wherein the oxidizing agent is chosen from peroxides and peracids.

15. The method of claim 14, wherein the oxidizing agent is a solution of hydrogen peroxide that is added at a flow rate of between V1/1000 and V1/10 ml/minute, V1 being the volume of the reaction medium containing the sulfated polysaccharide, to which the solution of hydrogen peroxide is added.

16. The method of claim 14, wherein the solution of oxidizing agent used in the second step is a solution of hydrogen peroxide that has a concentration of between 0.1% and 0.5% by weight and that is added to the reaction mixture at a flow rate of between V1/50 and V1/500 ml/minute.

17. The method of claim 16, wherein in the second step consisting of depolymerisation, the sulfated polysaccharide is present in the reaction mixture at a concentration of between 2 and 10 mg/ml of reaction mixture.

18. The method of claim 12, wherein the metal catalysts that can be used in the depolymerisation step are preferably chosen from $Cu^{++}$, $Fe^{+++}$ and $Cr^{+++}$ ions and the $Cr_2O_7^{2-}$ anion.

19. The method of claim 18, characterized in that the metal catalyst is present in the reaction mixture at a concentration of between $10^{-3}$ and $10^{-1}$ M.

20. The method of claim 1, wherein the preparation process comprises an additional step consisting of reduction of the sulfated polysaccharide derivative obtained using a reducing agent.

21. The method of claim 1, wherein the composition is used in combination with one or more growth factors.

22. The method of claim 1, wherein the composition exhibits a pro-angiogenic activity and is for cardiovascular therapy.

23. The method of claim 22, wherein said composition is for treating ischemia.

24. The method of claim 22, wherein said composition is for promoting revascularization in ischemic tissues and vascular modelling in thrombotic injuries.

\* \* \* \* \*